(12) United States Patent
Zlotnick et al.

(10) Patent No.: US 9,796,722 B1
(45) Date of Patent: Oct. 24, 2017

(54) HEPATITIS B VIRAL ASSEMBLY EFFECTORS

(71) Applicant: Indiana University Research and Technology Corporation, Indianapolis, IN (US)

(72) Inventors: Adam Zlotnick, Bloomington, IN (US); Lichun Li, Bloomington, IN (US); William W. Turner, Jr., Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 15/294,010

(22) Filed: Oct. 14, 2016

Related U.S. Application Data

(60) Provisional application No. 62/241,783, filed on Oct. 15, 2015.

(51) Int. Cl.
| | |
|---|---|
| C07D 487/04 | (2006.01) |
| A61K 47/00 | (2006.01) |
| A61K 31/519 | (2006.01) |
| A61K 45/06 | (2006.01) |

(52) U.S. Cl.
CPC .......... *C07D 487/04* (2013.01); *A61K 31/519* (2013.01); *A61K 45/06* (2013.01)

(58) Field of Classification Search
None
See application file for complete search history.

(56) References Cited

PUBLICATIONS

JP 10-114774. Published on Jun. 5, 1998. English machine translation.*

* cited by examiner

*Primary Examiner* — Anna Pagonakis
(74) *Attorney, Agent, or Firm* — Faegre Baker Daniels LLP

(57) ABSTRACT

Novel virus assembly effector compounds having a therapeutic effect against Hepatitis B viral infection are disclosed. Assembly effector molecules described herein can lead to defective viral assembly and also may affect other viral activities associated with chronic HBV infection. Also disclosed are pharmaceutical compositions including the disclosed compounds, methods of treatment of HBV infection, and a process to synthesize the disclosed compounds.

5 Claims, 2 Drawing Sheets

IU-11

IU-12

IU-11

IU-12

HEPATITIS B VIRAL ASSEMBLY EFFECTORS

CROSS REFERENCE TO RELATED APPLICATIONS

This application claims priority to U.S. Provisional Application No. 62/241,783, filed on Oct. 15, 2015, the entire disclosure of which is expressly incorporated herein by reference for all purposes.

STATEMENT REGARDING FEDERALLY SPONSORED RESEARCH

This invention was made with government support under AI067417 awarded by the National Institutes of Health. The government has certain rights in the invention.

BACKGROUND

Hepatitis B (HBV) causes viral Hepatitis that can further lead to chronic liver disease and increase the risk of liver cirrhosis and liver cancer (hepatocellular carcinoma). Worldwide, more than 2 billion people have been infected with HBV, around 360 million people are chronically infected and every year HBV infection causes more than one million deaths (World Health Organization, 2009). HBV can be spread by body fluids: e.g., from mother to child, by sex, and via blood products. Children born to HBV-positive mothers may be infected, unless vaccinated at birth.

At present, chronic HBV is primarily treated with nucleos(t)ides analogues (e.g., entecavir, tenofovir disoproxil fumarate (TDF)) that suppress the virus while the patient remains on treatment but do not eliminate the infection, even after many years of treatment. Once a patient starts taking nucleos(t)ide analogues, most must continue taking them or risk the possibility of a life threatening immune response to viral rebound. Further, nucleos(t)ide analogue therapy may lead to the emergence of antiviral drug resistance and, in rare cases, adverse events have been reported.

The only FDA approved alternative to nucleos(t)ide analogues is treatment with interferon-α (IFN-α) or pegylated interferon-α (PEG-IFN-α). Unfortunately, the adverse event incidence and profile of interferon-α can result in poor tolerability, and many patients are unable to complete therapy. Moreover, only a small percentage of patients are considered appropriate for interferon therapy, as only a small subset of patients who present with low viral loads and transaminitis greater than 2× the upper limit of normal are likely to have a sustained clinical response to a year's course of interferon therapy. As a result, interferon based therapies are used in only a small percentage of all diagnosed patients who elect for treatment.

Thus, current HBV treatments can range from palliative to benign neglect. Nucleos(t)ide analogues suppress virus production, treating the symptom, but leave the infection intact. Interferon-α has severe side effects and less tolerability among patients and is successful as a finite treatment strategy in only a small minority of patients.

SUMMARY

In certain aspects, the present disclosure provides pyrazolopyrimidine compounds having assembly effector properties against Hepatitis B virus. Such compounds may ultimately target multimerization of viral core proteins, which is central to HBV infection, where the core protein multimerizes into a shell, or capsid. The disclosed compounds may be considered CpAMs—core protein allosteric modifiers—which can lead to defective viral capsid assembly. Without being bound by any particular theory, such CpAMs may affect steps "upstream" of capsid assembly by altering the concentrations of Cp (core protein) available as dimer as compared to capsid or other multimeric forms. Disclosed compounds may noticeably affect functions upstream of viral assembly such as interfering with cccDNA transcription, RNA stability and/or protein-protein interactions.

In part, the disclosure is directed to pyrazolopyrimidines having the general structure described herein as Formula I and structural analogues thereof. In some embodiments, a pyrazolopyrimidine compound can have the structure of the compounds depicted in FIGS. 1A and 1B.

In another aspect, the disclosure provides pharmaceutical compositions that include at least one compound described herein and a pharmaceutically acceptable excipient.

In another aspect, the disclosure provides methods of treating HBV in a patient, where the methods include administering a therapeutically effective amount of at least one disclosed compound to the patient. In some embodiments, the patient is human. In some embodiments, the pharmaceutical composition is administered to the subject as part of a Hepatitis B (HBV) combination therapy together with at least one additional antiviral. The at least one additional antiviral can include at least one of interferon-α, pegylated interferon-α, interferon-α-2b, entecavir, tenofovir, lamivudine, adefovir dipivoxil, telbivudine and at least one assembly effector. In certain embodiments, the at least one assembly effector includes at least one heteroaryldihydropyrimidine. When administered as part of a combination therapy, the pharmaceutical composition may be administered to the subject before, concurrently with, or after the at least one additional antiviral.

In other aspects, use of a disclosed compound in the manufacture of medicaments for treatment of Hepatitis B (HBV) infection is described.

In yet another aspect, a process for preparing a compound described herein is provided.

DEFINITIONS

Figure 1A:
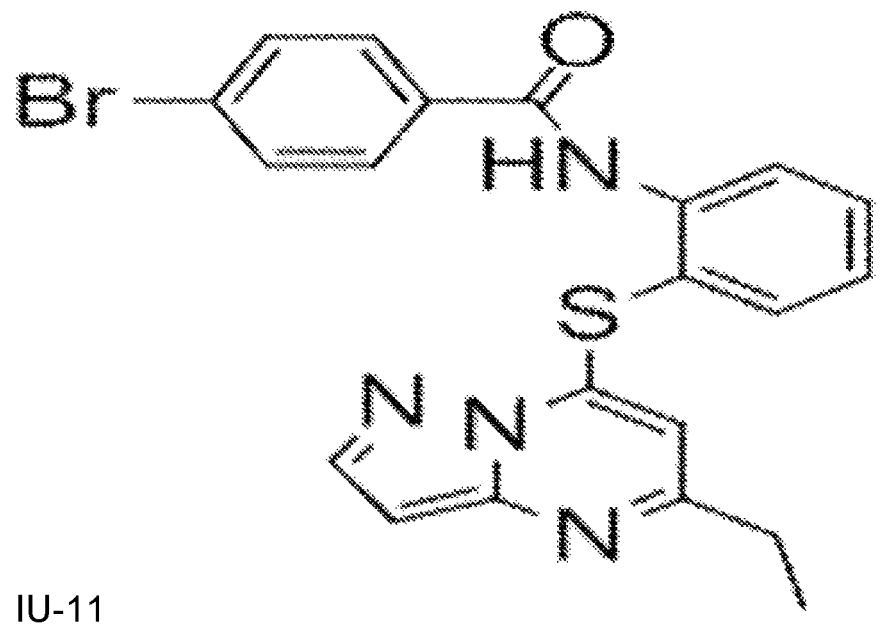
FIGS. 1A-1B illustrates structural analogues of disclosed compounds having antiviral properties, in accordance with an embodiment of the present invention.

The features and other details of the disclosure will now be more particularly described. Before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

As intended herein, the terms "a" and "an" include singular as well as plural references unless the context clearly dictates otherwise. For example, the term "an assembly effector" can include one or more such effectors.

"Treating" includes any effect, e.g., lessening, reducing, modulating, or eliminating, that results in the improvement of the condition, disease, disorder and the like.

The term "alkenyl" as used herein refers to an unsaturated straight or branched hydrocarbon having at least one carbon-carbon double bond, such as a straight or branched group of 2-6 or 3-4 carbon atoms, referred to herein for example as $C_{2-6}$ alkenyl, and $C_{3-4}$ alkenyl, respectively. Exemplary alkenyl groups include, but are not limited to, vinyl, allyl, butenyl, pentenyl, etc.

The term "alkoxy" as used herein refers to a straight or branched alkyl group attached to an oxygen (alkyl-O—). Exemplary alkoxy groups include, but are not limited to, groups with an alkyl group of 1-6 or 2-6 carbon atoms, referred to herein as $C_{1-6}$ alkoxy, and $C_2$-$C_6$ alkoxy, respectively. Exemplary alkoxy groups include, but are not limited to methoxy, ethoxy, isopropoxy, etc.

The term "alkenyloxy" used herein refers to a straight or branched alkenyl group attached to an oxygen (alkenyl-O). Exemplary alkenoxy groups include, but are not limited to, groups with an alkenyl group of 3-6 carbon atoms referred to herein as $C_{3-6}$ alkenyloxy. Exemplary "alkenoxy" groups include, but are not limited to allyloxy, butenoxy, etc.

The term "alkynyloxy" used herein refers to a straight or branched alkynyl group attached to an oxygen (alkynyl-O)). Exemplary alkynyloxy groups include, but are not limited to, propynyloxy.

The term "alkyl" as used herein refers to a saturated straight or branched hydrocarbon, such as a straight or branched group of 1-6, 1-4, or 1-3 carbon atoms, referred to herein as $C_1$-$C_6$ alkyl, $C_1$-$C_4$ alkyl, and $C_1$-$C_3$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 3-methyl-2-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkynyl" as used herein refers to an unsaturated straight or branched hydrocarbon having at least one carbon-carbon triple bond, such as a straight or branched group of 2-6, or 3-6 carbon atoms, referred to herein as $C_2$-$C_6$ alkynyl, and $C_3$-$C_6$ alkynyl, respectively. Exemplary alkynyl groups include, but are not limited to, ethynyl, propynyl, butynyl, pentynyl, hexynyl, methylpropynyl, etc.

The term "bridged cycloalkyl", as used herein, is defined as a monocyclic 4- to 7-membered cycloalkyl group in which two non-adjacent atoms are linked by a $CH_2$ or $CH_2CH_2$ group. A "bridged cycloalkyl" may be fused to one or more phenyl, partially unsaturated, or saturated rings. Examples of bridged cycloalkyl groups include but are not limited to bicyclo[2.2.1]heptane, bicyclo[2.2.2]octane, bicyclo[2.2.2]octene etc.

The term "carbonyl" as used herein refers to the radical —C(O)—. The term "cyan" as used herein refers to the radical —CN.

The term "cycloalkoxy" as used herein refers to a cycloalkyl group attached to an oxygen (cycloalkyl-O—).

The term "cycloalkyl" as used herein refers to a monocyclic saturated or more particularly unsaturated hydrocarbon group of, for example, 3-6, or 4-6 carbons, referred to herein, e.g., as $C_{3-6}$ cycloalkyl or $C_{4-6}$ cycloalkyl, and derived from a cycloalkane. Exemplary cycloalkyl groups include, but are not limited to, cyclohexane, cyclohexene, cyclopentane, cyclobutane or, cyclopropane.

The terms "halo" or "halogen" as used herein refer to F, Cl, Br, or I.

The terms "heteroaryl" as used herein refers to a monocyclic aromatic 4-6 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridyl, and pyrimidinyl.

The terms "heterocyclyl" or "heterocyclic group" are art-recognized and refer to saturated or partially unsaturated 4- to 7-membered ring structures, whose ring structures include one to three heteroatoms, such as nitrogen, oxygen, and sulfur. A heterocyclyl may be fused to one or more phenyl, partially unsaturated, or saturated rings. Examples of heterocyclyl groups include but are not limited to pyrrolidine, piperidine, morpholine, thiomorpholine, and piperazine.

The term "heterocyclylalkoxy" as used herein refers to a heterocyclyl-alkyl-O— group.

The term "heterocyclyloxyalkyl" refers to a heterocyclyl-O-alkyl- group.

The term "heterocyclyloxy" refers to a heterocyclyl-O— group. The term "heteroaryloxy" refers to a heteroaryl-O— group.

The terms "hydroxy" and "hydroxyl" as used herein refers to the radical —OH.

The term "oxo" as used herein refers to the radical =O.

"Pharmaceutically acceptable" or "pharmacologically acceptable" include molecular entities and compositions that do not produce an adverse, allergic or other untoward reaction when administered to an animal, or a human, as appropriate. For human administration, preparations should meet sterility, pyrogenicity, general safety and purity standards such as, for example, those standards required by the FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, such as mice, rats, other rodents, rabbits, dogs, cats, swine, cattle, sheep, horses, or primates, and humans. The compounds of the invention can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the invention is desirably a mammal in which treatment of hepatitis B is desired.

"Modulation" includes antagonism (e.g., inhibition), agonism, partial antagonism and/or partial agonism.

In the present specification, the term "therapeutically effective amount" means the amount of the subject compound that will elicit the biological or medical response of a tissue, system, animal or human that is being sought by the researcher, veterinarian, medical doctor or other clinician. The compounds of the invention are administered in therapeutically effective amounts to treat a disease.

The term "pharmaceutically acceptable salt(s)" as used herein refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and/or double bonds and, therefore, exist as stereoisomers, such as geometric isomers, enantiomers or diastereomers. The term "stereoisomers" when used herein includes all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

The compounds of the disclosure may contain one or more chiral centers and/or double bonds and, therefore, exist as geometric isomers, enantiomers or diastereomers. The enantiomer and diastereomers may be designated by the symbols "(+)," "(−)." "R" or "S," depending on the configuration of substituents around the stereogenic carbon atom, but the skilled artisan will recognize that a structure may denote a chiral center implicitly. Geometric isomers, resulting from the arrangement of substituents around a carbon-carbon double bond or arrangement of substituents around a cycloalkyl or heterocyclic ring, can also exist in the compounds of the present invention. The symbol denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The term "stereoisomers" when used herein consists of all geometric isomers, enantiomers or diastereomers. The present invention encompasses various stereoisomers of these compounds and mixtures thereof Individual enantiomers and diastereomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography, and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well-known methods, such as chiral-phase gas chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a polymorph. In another embodiment, the compound is in a crystalline form.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$ respectively. For example, a compound of the invention may have one or more H atom replaced with deuterium.

Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly useful due to their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al, Nature Reviews Drug Discovery 2008, 7, 255). For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as (C1-C8)alkyl, (C2-C12)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as (3-dimethylaminoethyl), carbamoyl-($C_1$-$C_2$)alkyl, N,N-di($C_1$-$C_2$) alkylcarbamoyl-($C_1$-$C_2$)alkyl and piperidino-, pyrrolidino- or morpholino($C_2$-$C_3$)alkyl.

Similarly, if a compound of the invention contains an alcohol functional group, a prodrug can be formed by the replacement of the hydrogen atom of the alcohol group with a group such as ($C_1$-$C_6$)alkanoyloxymethyl, 1-(($C_{1-6}$)alkanoyloxy)ethyl, 1-methyl-1-(($C_{1-6}$)alkanoyloxy)ethyl ($C_{1-6}$)alkoxycarbonyloxymethyl, N—($C_1$-$C_6$) alkoxycarbonylaminomethyl, succinoyl, ($C_{1-6}$)alkanoyl, α-amino ($C_{1-4}$) alkanoyl, arylacyl and α-aminoacyl, or α-aminoacyl-α-aminoacyl, where each α-aminoacyl group is independently selected from the naturally occurring L-amino acids, P(O) (OH)$_2$, —P(O)(O($C_1$-$C_6$)alkyl)$_2$ or glycosyl (the radical resulting from the removal of a hydroxyl group of the hemiacetal form of a carbohydrate).

If a compound of the invention incorporates an amine functional group, a prodrug can be formed, for example, by creation of an amide or carbamate, an N-acyloxyakyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplicio, et al., *Molecules* 2008, 13, 519 and references therein.

DETAILED DESCRIPTION

Certain classes of compounds, such as those described herein, may activate assembly of the viral capsid independent of the normal nucleating signals, e.g. act as core protein allosteric modulators (CpAMs) having an effect against HBV. For example, the disclosed compounds may activate assembly of the viral capsid independent of the normal nucleating signals.

Hepatitis B virus consists of an envelope, a nucleocapsid core, viral DNA and reverse transcriptase (RT). Infection starts upon virus entry into the host. The viral core enclosing the viral DNA and the RT are transferred to the cytoplasm of the host and to the host's nucleus, a process during which the circular and partially double stranded viral DNA is released from the viral core.

Inside the nucleus, the viral DNA is converted into a covalently-closed circular DNA (cccDNA), which codes for a pregenomic RNA (pgRNA) and other mRNAs. The pregenomic RNA, exported to the cytoplasm, codes for core protein and the reverse transcriptase. Encapsidation of the pregenomic RNA and the reverse transcriptase by core protein results in the formation of immature HBV cores which maturate as the pregenomic RNA is reverse transcribed to the circular and partially double stranded DNA, completing the cycle.

Central to HBV infection is the assembly of the viral core. The capsid itself is a complex of 120 copies of core protein homodimers that spontaneously self-assemble. In the presence of assembly effectors (AE), capsid assembly begins with an AE•Cp (Assembly effector•Core protein) complex instead of waiting for the biological RT•pgRNA nucleating complex; the resulting capsid is thus defective. Core protein allosteric modulators (CpAMs) can leverage consumption of a few molecules needed for nucleation to consume, for example, up to 117 Cp dimers. To nucleate assembly, in some embodiments, CpAMs may have one or both activities of substantially interacting with (e.g., binding to) Cp dimers, thereby activating assembly; and substantially binding or interacting with capsids at e.g., a higher affinity as compared to binding to the Cp dimer.

The core proteins also have roles upstream of capsid assembly and are associated with nuclear cccDNA and affect their stability and transcription; they are involved in export of the pregenomic RNA from the nucleus.

For example, the compounds provided herein may affect virus assembly by interacting with core protein dimers as well as capsids, and/or may affect core protein activity upstream of capsid assembly. Defective assembly can immediately suppress virus production. Suppressed Cp activity upstream of assembly can also interfere with activities of the virus required for stability of the infection itself. For example, the provided compounds may successfully treat HBV with a finite course of therapy as opposed to the potentially life-long therapy available with current nucleos (t)ide analogues. Finite therapy would result from a loss of new viral proteins and mRNA resulting from epigenetic modification of the viral cccDNA, as well as a reduction in new infectious virions. In other words, disclosed compounds may activate viral capsid assembly independent of the normal nucleating signals leading to defective assembly: capsid assembly begins with an AE•Cp complex instead of waiting for the biological RT•pgRNA nucleating complex. The resulting capsid or aberrant complex, for example, cannot support production of new virions. In some embodiments, disclosed compounds may leverage consumption of a few molecules needed for nucleation to consume up to 120 Cp dimers. Disclosed compounds may for example, alter the concentration of Cp (core protein), likely required for activities upstream of capsid assembly. Suppressing Cp activity upstream of assembly interferes with the Cp interactions with the viral reservoir (cccDNA). This may lead to clearance of the infection by reduction of viral proteins and cccDNA activity.

In certain embodiments, compounds of Formula I and pharmaceutically acceptable salts and stereoisomers thereof are provided:

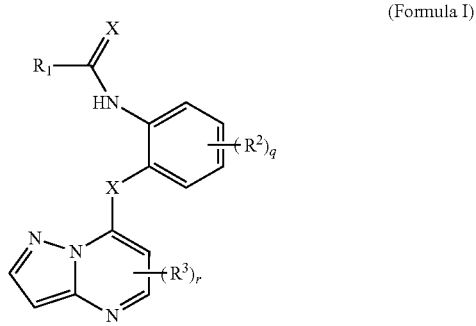

(Formula I)

wherein
each X is independently S or 0;
r is 0, 1, 2, 3 or 4;
q is 0, 1, 2, 3, or 4;
$R^1$ is selected from the group of alkyl, aryl; —NH-alkyl, or —NH-phenyl; and
$R^2$ and $R^3$ are each independently selected for each occurrence from the group of H, alkyl, aryl, electron donating, and electron-withdrawing groups.

Contemplated alkyl and aryl groups of $R^1$, $R^2$, and $R^3$ may be each independently optionally substituted with one or more substituents independently selected from the group of halogen, hydroxyl, nitro, cyano, carboxy, amino, ether, oxo, carbonyl-alkyl, carbonyl-alkoxy, alkoxy-carbonyl, carbonyl-amino, amino-carbonyl, sulfonyl-alkyl, sulfonyl-amino, sulfonyl-amino-alkyl, sulfonyl-amino-dialkyl, amino-sulfonyl, alkyl-sulfonyl, alkyl-sulfonyl-amino, amino-dialkyl, amino-cycloalkyl, phenyl, alkyl-amino, alkyl-carbonyl, sulfonyl-alkyamino-dialkyl, etc.

Electron donating, and electron-withdrawing groups may be one or more of halogen, hydroxyl, nitro, cyano, carboxy, amino, ether, oxo, carbonyl-alkyl, carbonyl-alkoxy, alkoxy-carbonyl, carbonyl-amino, amino-carbonyl, sulfonyl-alkyl, sulfonyl-amino, sulfonyl-amino-alkyl, sulfonyl-amino-dialkyl, amino-sulfonyl, alkyl-sulfonyl, alkyl-sulfonyl-amino, amino-dialkyl, amino-cycloalkyl, phenyl, alkyl-amino, alkyl-carbonyl, sulfonyl-alkyamino-dialkyl, etc.

In an embodiment, $R^2$ and $R^3$ are each independently selected from the group of H, halogen, $C_{1-6}$ alkyl, $C_{1-6}$ alkoxy; and —NR'—C(O)—$C_{1-6}$ alkyl (wherein R' is H or $C_{1-6}$ alkyl).

In another embodiment, moiety $R_1$ may be selected from alkyl, aryl, NH-alkyl and NH-aryl, wherein alkyl, aryl, NH-alkyl and NH-aryl groups may be optionally substituted with one or more substituents selected from the group of halogen, hydroxyl, nitro, cyano, carboxy, amino, ether, oxo, carbonyl-alkyl, carbonyl-alkoxy, alkoxy-carbonyl, carbonyl-amino, amino-carbonyl, sulfonyl-alkyl, sulfonyl-amino, sulfonyl-amino-alkyl, sulfonyl-amino-dialkyl, amino-sulfonyl, alkyl-sulfonyl, alkyl-sulfonyl-amino, amino-dialkyl, amino-cycloalkyl, phenyl, alkyl-amino, alkyl-carbonyl, sulfonyl-alkyamino-dialkyl, etc.

Figure 1B:
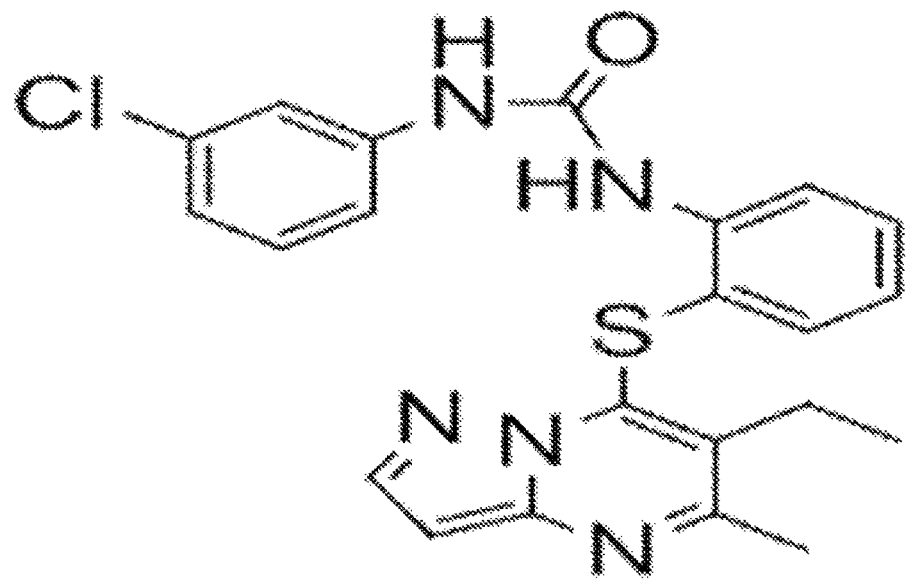

Some examples of pyrazolopyrimidines molecules having a structure of Formula I are provided in FIGS. 1A-1B.

Figure 2:
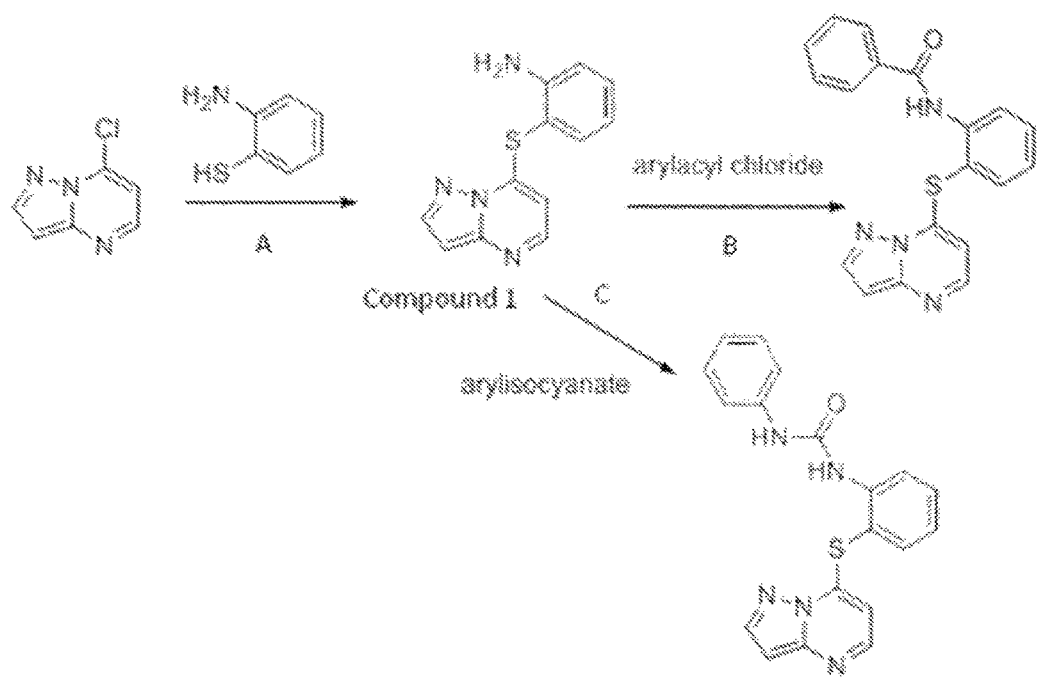
FIG. 2 illustrates a general synthetic scheme for synthesizing disclosed compounds having antiviral properties, in accordance with an embodiment of the present invention.

In a second aspect of the invention, a method for the synthesis of this class of CpAMs is provided. In an embodiment, the method may follow Synthetic Scheme 1, as illustrated in FIG. 2. Compound 1 from the synthetic scheme 1, is prepared in synthetic step A, from 5-chloro pyrazolo-pyrimidine by addition of thioaniline in an organic solvent. Thereafter, at synthetic step B, addition of aryl acyl chloride leads to formation of exemplary form IU-11, a structural analogue of a pyrazolopyrimidine molecule having antiviral properties. At synthetic step C of synthetic scheme 1, addition of arylisocyanate leads to formation of exemplary form IU-12, a structural analogue of a pyrazolopyrimidine molecule having antiviral properties.

In a further aspect, a method for treating HBV infection (e.g. an acute or chronic HBV infection) in a patient is provided. The method includes administering to the subject a pharmaceutical composition comprising a therapeutically effective amount of a disclosed compound.

For use in accordance with this aspect, the appropriate dosage is expected to vary depending on, for example, the particular compound employed, the mode of administration, and the nature and severity of the infection to be treated as well as the specific infection to be treated and is within the purview of the treating physician. Usually, an indicated administration dose may be in the range between about 0.1 to about 15 mg/kg body weight. In some cases, the administration dose of the compound may be less than 10 mg/kg body weight. In other cases, the administration dose may be less than 5 mg/kg body weight. In yet other cases, the administration dose may be in the range between about 0.1 to about 1 mg/kg body weight. The dose may be conveniently administered once daily, or in divided doses up to, for example, four times a day or in sustained release form.

A compound may be administered by any conventional route, in particular: enterally, topically, orally, nasally, e.g. in the form of tablets or capsules, via suppositories, or parenterally, e.g. in the form of injectable solutions or suspensions, for intravenous, intra-muscular, sub-cutaneous, or intra-peritoneal injection. Suitable formulations and pharmaceutical compositions will include those formulated in a conventional manner using one or more physiologically acceptable carriers or excipients, and any of those known and commercially available and currently employed in the clinical setting. Thus, the compounds may be formulated for oral, buccal, topical, parenteral, rectal or transdermal administration or in a form suitable for administration by inhalation or insufflation (either orally or nasally).

For oral administration, pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). Tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). Preparations may also contain buffer salts, flavoring, coloring and sweetening agents as appropriate.

Preparations for oral administration may also be suitably formulated to give controlled-release or sustained release of the active compound(s) over an extended period. For buccal administration the compositions may take the form of tablets or lozenges formulated in a conventional manner known to the skilled artisan.

A compound may also be formulated for parenteral administration by injection, e.g. by bolus injection or continuous infusion. Formulations for injection may be presented in unit dosage form; e.g. in ampoules or in multi-dose containers, with an added preservative. The compositions may take such forms as suspensions, solutions or emulsions in oily or aqueous vehicles, and may contain additives such as suspending, stabilizing and/or dispersing agents. Alternatively, the compound may be in powder form for constitution with a suitable vehicle, e.g. sterile pyrogen-free water, before use. Compounds may also be formulated for rectal administration as suppositories or retention enemas, e.g. containing conventional suppository bases such as cocoa butter or other glycerides.

In some cases, disclosed compounds may be administered as part of a combination therapy in conjunction with one or more antivirals. Example antivirals include nucleos(t)ide analogues such as entecavir, tenofovir, lamivudine, adefovir dipivoxil, and telbivudine, interferon-α, pegylated interferon-α, and interferon-α-2b, and other assembly effectors, including but not limited to heteroaryldihydropyrimidines (HAPs) such as methyl 4-(2-chloro-4-fluorophenyl)-6-methyl-2-(pyridin-2-yl)-1,4-dihydropyrimidine-5-carboxylate. This may involve administering to a subject a first amount of a disclosed compound in combination with a second amount of an antiviral, wherein the first and second amounts together comprise a pharmaceutically effective amount. The first amount, the second amount, or both may be the same, more, or less than effective amounts of each compound administered as monotherapies. Therapeutically effective amounts of disclosed compound and antiviral may be co-administered to the subject, i.e., administered to the subject simultaneously or separately, in any given order and by the same or different routes of administration. In some instances, the disclosed pyrazolopyrimidine compounds may be administered first, for example one or more days or weeks prior to initiation of administration of the antiviral. Moreover, additional drugs may be given in conjunction with the above combination therapy.

Example 1—Assembly Effector Activity Assay

A screening assay for assembly effector activity was conducted based on a fluorescence quenching assay developed in the Zlotnick lab (see, e.g., Stray et al. (2006), Nature Biotechnology 24(3):358-62, and Zlotnick et al. (2007), Nature Protocols 2(3):490-98, each of which is incorporated herein by reference in its entirety). Briefly, a Cp mutant is specifically labeled with a fluorescent dye. In the dimeric state, fluorescence is intense. However, when the Cp assembles, the dye molecules accumulate at fivefold and quasi-sixfold vertices to self-quench by up to 95%. In the high throughput screen, the Cp concentration is chosen so that addition of NaCl, typically 150 mM or 300 mM, is sufficient to induce about 25% assembly. The pyrazolopyrimidine structural analogues (first structure in FIG. 1A (IU-11)A and second structure in FIG. 1B (IU-12)B) showed strong assembly activating activity. After 24 hrs, the pyrazolopyrimidine structural analogue of FIG. 1A increased capsid formation by 95% and that of FIG. 1B by 82%.

All of the compositions and methods disclosed and claimed herein can be made and executed without undue experimentation in light of the present disclosure. While the compositions and methods have been described in terms of embodiments, it will be apparent to those of skill in the art that variations maybe applied to the compositions and methods and in the steps or in the sequence of steps of the methods described herein without departing from the concept, spirit and scope herein. More specifically, certain agents that are both chemically and physiologically related may be substituted for the agents described herein while the same or similar results would be achieved. All such similar substitutes and modifications apparent to those skilled in the art are deemed to be within the spirit, scope and concept as defined by the appended claims.

What is claimed is:

1. A compound of Formula I

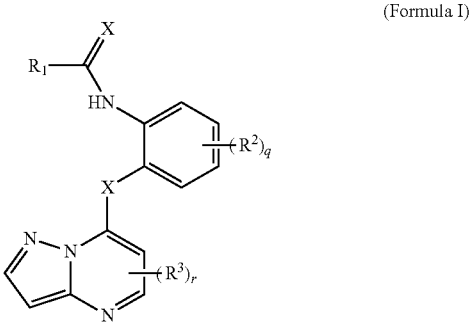

(Formula I)

or a pharmaceutically acceptable salt or stereoisomer thereof, wherein each X is independently S or O;

r is 0, 1, 2, 3 or 4;

q is 0, 1, 2, 3, or 4;

$R^1$ is selected from the group of alkyl, aryl; —NH-alkyl, and —NH-phenyl, wherein the alkyl, aryl, —NH—alkyl, or —NH-phenyl is optionally substituted with one or more halogen substituents; and $R^2$ and $R^3$ are independently selected for each occurrence from the group of hydrogen, alkyl, aryl, alkoxy, —NR'—C(O)—$C_{1-6}$ alkyl wherein R' is H or $C_{1-6}$ alkyl, an electron donating group, and an electron-withdrawing group, wherein the alkyl and aryl groups of $R^1$, $R^2$, and $R^3$ may be each independently optionally substituted with one or more substituents selected from the group of hydrogen, halogen, hydroxyl, nitro, cyano, carboxy, amino, ether, oxo, carbonyl-alkyl, carbonyl-alkoxy, alkoxy-carbonyl, carbonyl-amino, amino-carbonyl, sulfonyl-alkyl, sulfonyl-amino, sulfonyl-amino-alkyl, sulfonyl-amino-dialkyl, amino-sulfonyl, alkyl-sulfonyl, alkyl-sulfonyl-amino, amino-dialkyl, amino-cycloalkyl, phenyl, alkyl-amino, alkyl-carbonyl, and sulfonyl-alkyamino-dialkyl, and wherein the electron donating group and the electron-withdrawing group are independently selected for each occurrence from the group of halogen, hydroxyl, nitro, cyano, carboxy, amino, ether, oxo, carbonyl-alkyl, carbonyl-alkoxy, alkoxy-carbonyl, carbonyl-amino, amino-carbonyl, sulfonyl-alkyl, sulfonyl-amino, sulfonyl-amino-alkyl, sulfonyl-amino-dialkyl, amino-sulfonyl, alkyl-sulfonyl, alkyl-sulfonyl-amino, amino-dialkyl, amino-cycloalkyl, phenyl, alkyl-amino, alkyl-carbonyl, and sulfonylalkyaminodialkyl.

2. The compound of claim 1, wherein $R^2$ and $R^3$ are each independently selected from the group of H, halogen, $C_{1-6}$ alkyl, $C_{1-6}$ alkoxy, and —NR'—C(O)—$C_{1-6}$ alkyl, wherein R' is H or $C_{1-6}$ alkyl.

3. The compound of claim 1, wherein the compound has the structure:

4. The compound of claim 1, wherein the compound has the structure:
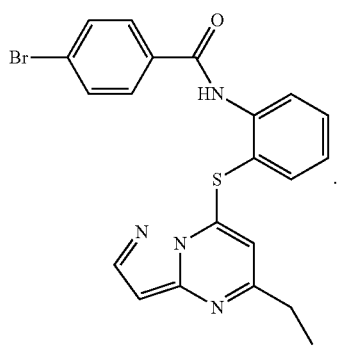 [SMILES: CCC1=N/C(=C/C=N)NC(Sc2ccccc2NC(=O)c2ccc(Br)cc2)=C1]
5. A pharmaceutical composition comprising a compound of claim 1 and a pharmaceutically acceptable excipient.
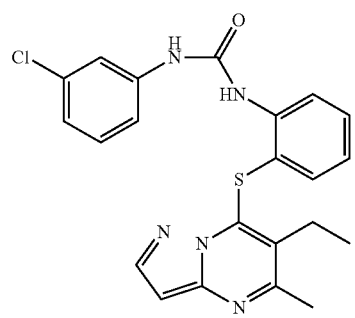
* * * * *